United States Patent [19]

Siu

[11] Patent Number: 5,424,838
[45] Date of Patent: Jun. 13, 1995

[54] MICROELECTRONICS INSPECTION SYSTEM

[76] Inventor: Bernard Siu, 732 N. Diamond Bar Blvd., Diamond Bar, Calif. 91765

[21] Appl. No.: 25,442

[22] Filed: Mar. 1, 1993

[51] Int. Cl.$^6$ ............................................. G01B 11/24
[52] U.S. Cl. .................... 356/394; 356/237; 356/375; 356/376; 250/562; 250/572
[58] Field of Search ............. 356/394, 237, 375, 376; 348/126; 250/572, 561, 562, 563

[56] References Cited

U.S. PATENT DOCUMENTS

| | | | |
|---|---|---|---|
| 3,737,226 | 6/1973 | Shank | 355/67 |
| 4,284,353 | 8/1981 | Yoshida | 250/227.28 |
| 4,427,880 | 1/1984 | Kanade | 250/222.1 |
| 4,508,452 | 4/1985 | DiMatteo | 356/375 |
| 4,568,835 | 2/1986 | Imamura | 250/572 |
| 4,688,939 | 8/1987 | Ray | 250/572 |
| 4,695,163 | 9/1987 | Schachar | 356/369 |
| 4,791,482 | 12/1988 | Barry | 358/107 |
| 4,816,686 | 3/1989 | Hara | 356/237 |
| 4,876,455 | 10/1989 | Sanderson | 250/560 |
| 4,882,498 | 11/1989 | Cochran | 250/571 |
| 4,972,493 | 11/1990 | Chemaly | 382/8 |
| 4,988,202 | 1/1991 | Nayar et al. | 356/394 |
| 5,027,418 | 6/1991 | Ikegaya et al. | 250/562 |
| 5,030,008 | 7/1991 | Scott et al. | 356/394 |
| 5,032,735 | 7/1991 | Kobayashi | 250/572 |
| 5,088,828 | 2/1992 | Doemens | 250/227.28 |
| 5,267,217 | 11/1993 | Tokura et al. | 356/237 |
| 5,302,836 | 4/1994 | Siu | 356/237 |

FOREIGN PATENT DOCUMENTS 0452905 10/1991 European Pat. Off. ............ 250/572

*Primary Examiner*—Rolf Hille
*Assistant Examiner*—Minhloan Tran
*Attorney, Agent, or Firm*—Leo R. Carroll

[57] ABSTRACT

The present invention is directed to an improved system for inspection of microelectronic assemblies, including chips and interconnection elements such as wires, ball bonds, and wedge bonds contained therein. This system includes a high speed illumination subsystem, a dual magneification video camera sensor subsystem, a commercial machine vision system supported by a video display and printer, a three dimensional transport stage for moving the microcircuit under inspection, and a computer controller for operational control under unique software of all of the above system elements. The illumination subsystem includes formation of multiple light rings starting with light generated by a tungsten lamp, collimation by a condenser lens, then passage through a liquid crystal light valve having a plurality of circular active transmission areas. A projector lens receives both rings of light and projects the larger ring on an ellipsoidal reflector which redirects the light onto the microcircuit at a large off-verical axis angle which has been found to provide optimal contrast for rounded bodies such a wires and ball bonds. The projector lens also focuses the more narrow beam of light on a toroidal Fresnel lens mounted above the microcircuit, and which also redirects the beam at a smaller off-vertical axis angle which has been found provide optimal contrast for wedge shaped bonds. By alternating the light transmission through each of these rings at high speed, defective reflective signatures of interconnect wires, ball bonds, bond wedges and microcircuit chips can be captured by the an objective lens and mirror reflected to the light responsive camera system.

17 Claims, 7 Drawing Sheets

MICROELECTRONICS INSPECTION SYSTEM

BACKGROUND OF THE INVENTION

1. Technical Field

This invention relates generally to methods and apparatus for high speed inspection of microelectronic device connections, and in particular to a total automatic system used to illuminate, image capture and fault detect interconnect wire, wire bonds, ball bonds, and wedge bonds. This invention is related to co-pending applications U.S. Ser. No. 914,541, now U.S. Pat. No. 5,302,836, and co-pending U.S. Application No. 08/025,441 which describe earlier subsystem portions of this system. Application 914,541 discloses a multiple ring illumination system comprised of separate cylindrical fiber optics bundles which are physically angled and shutter switched to provide light at incident angles optimal for improved visual discrimination of the interconnect elements against a similar background. See FIGS. 3-6 of No. 914,541. Application 08/025,441 improves operational speed of the illumination subsystem by replacing the fiber optics and shutter portions with a liquid crystal light valve assembly. This invention adds a novel image capture subsystem, and further incorporates both subsystems with other elements necessary to comprise a total inspection system.

Typically, gold wires, gold bonds, and gold terminations are viewed against a gold background by manual inspection under a microscope. Since the field of view is normally less than one-eighth (⅛) of an inch, uniform illumination is needed to highlight the area of interest. The most common uniform illumination source is a circular ring light directing illumination perpendicularly or at a slight angle off normal onto the surface to be inspected. While this type of lighting works rather well under a microscope, the glares and shiny hot spots from the gold connections and the reflective backgrounds are often ignored by the operators, as they tend to interpolate, or "fill in" dark missing fragments of the images. Variations in such human judgments are a cause of inconsistent inspection results. For instance, the incremental fill in of a dark position on a wire may actually hide a break in the wire at that point.

With the recent development of machine vision technologies, attempts were made to inspect these gold interconnects and gold terminations per Mil-Std-883 Method 2017. Machine vision technologies, however, have not reached the sophistication of ignoring hot spots or filling in fragments in a random basis as a human being could. The approach, therefore is to develop an illumination technique, capable of isolating the specular interconnect wires, ball bonds, bond wedges and chips exclusively from its reflective backgrounds. In other words, provide a better contrast between the object of interest from its neighboring background. In addition, the illumination techniques must be fast enough to support machine vision technologies used for the image acquisition and processing of microelectronics inspection tasks.

2. Background Art

Early improvements in inspection methods were concerned with better work-piece illumination, more accurate location, object image acquisition, flaw identification, recognition and finally rejection against given criterion. The focus of evolutionary inventive steps in these directions may be seen by overview of the following patents:

The need for diffused lighting to reduce reflections and shadows in close-up photography has been long recognized. Shank, in U.S. Pat. No. 3,737,226 discloses apparatus in which an indirect light source illuminates a small object through a series of pyramidal reflectors. Light is thus diffused around four sides of the object before reflection to a camera. This invention was for close-up photography and would have limited value for high speed inspection of microelectronic elements.

Kanade et al., in U.S. Pat. No. 4,427,880, provide an array of discrete light-emitting sources which are used to sequentially illuminate a symmetrical work piece object. Reflections are focused on a light responsive position sensor so as to provide continuous indications of distance, surface orientation and curvature of the object. Details of surface geometry are not provided. This approach is most effective for measuring distance if the reflective surface is flat. Based on the position of the reflected light spots on the surface, the distance between the surface and the optical sensor can be calculated and determined. The system does not use continuous illumination for visual identification of the object and its orientation. U.S. Pat. No. 4,508,452 to DiMatteo et al provides for determining the surface profile of an object by projecting a pre-coded pattern onto the surface. By matching the newly acquired image pattern to a pre-determined image pattern, the profile of the newly acquired image can be extracted. An object surface is scanned by a moving projector and subdivided into the large number of coded sections. Comparisons are made of progressive photographs of the work-piece with those of a standard reference surface. The entire surface of an object may therefore be mapped. The system is not applicable to improving contrast between very small three dimensional objects, such as wires, and the reflective background.

Imamura et al. in U.S. Pat. No. 4,568,835, detects foreign matter such as dust particles on a plane substrate by means of scattering of the reflections from a laser beam. As a specimen work-piece such as a photomask is scanned by an oblique incidence laser illumination beam, reflections from foreign materials are less directly scattered than are those from the edges of the circuit pattern. The illumination incidence angle is 80 to 60 degrees off normal, with a portion of the beam being reflected from the substrate surface while the remainder is refracted into the substrate medium from which it is internally reflected then externally scattered outward. This approach does not consider circular illumination used with a highly reflective, low refractive background medium.

In a different surface measurement application, Schachar, in U.S. Pat. No. 4,695,163, determines the contour of a cornea by scanning the surface with coherent light from different positions along a rectilinear path. Reflections received by detectors along the track are maximally polarized when the incidence angle equals Brewsters's angle. From a knowledge of the index of refraction of the medium and of Brewster's angle, the relative spacial locations of points over the surface may be determined. The system should provide slow but precise information when a refracting medium is under inspection, but will have limited utility with highly reflective objects.

An object locating system for use with robotic systems is described in U.S. Pat. No. 4,791,482 to Barry et al. The system projects a known geometrical image from a light source onto the surface of an object. The plane of the image on the object is determined by finding a normal to the surface from known geometrical relationships. Comparison of normals at different surface points are used to calculate distances and angles between the points. Gaussian images are generated for comparison between referenced objects and the unit under test.

In the field of solder joint inspection systems, Sanderson in U.S. Pat. No. 4,876,455 discloses a fiber optic solder joint inspection approach, in which light from multiple sources is reflected from a specular object to a fixed array of transducers. The individual light sources are derived from a single source which is scanned and piped to a plurality of optical fibers which lead to individual openings spaced around a semicircular illumination frame. For a given surface attitude, reflections to the fixed transducers will result from only one illumination source, assuming essentially specular reflection from the surface. Given known surface features of the object, an approximate reconstruction of the shape is made. The point source is usable with solder joint fillet inspection, but not with the variably curved and positioned wiring connections of microelectronic assemblies.

A related invention, U.S. Pat. No. 4,988,202 to Nayar et al, extends the above approach to include generation of an Extended Gaussian Image representation of a solder joint which is then evaluated as to acceptability.

A system for inspection of the uniformity of the surface of a flat circuit board component such as a dual inline package, employing computer vision is taught by Chemaly in U.S. Pat. No. 4,972,493. Illumination is provided by low angular light at the surface edge. Anomalies on the flat surface of dual in-line packages are inspected for pits, holes, blisters, grease, marks, chips and cracks. Marks on the surface are distinguished from planned surface irregularities by comparison of grey scale brightness. The two directional lighting is not developed for specular surfaces such as wires, bonds and wedges.

Inspection of the circuit board components when soldered in place is taught by Ikegaya et al. in U.S. Pat. No. 5,027,418. Component lighting is provided by a standard ring illuminator positioned normal to the board. Board masking is provided to make an assessment of soldering condition independent of component lead placement on the circuit board lands.

It may be noted that none of the above inspection systems treat identification and inspection of variably curved and placed circuit elements such as microelectronic wires and bonds. Further, none teach the use or advantages of dual annular illumination sources, each disposed at different angular relationships with respect to normal, each of which provides optimal viewing contrasts for different classes of microelectronic wires and bonds relative to their similar backgrounds.

DISCLOSURE OF INVENTION

The present invention is directed to an improved system for inspection of microelectronic assemblies, including the interconnect wires, ball bonds, and wedge bonds contained therein. Inspection of such devices today often uses a comparative method. Magnified projections of a reference sample and of the unit under inspection are visually compared on adjacent or split screens. The human inspector visually does the comparison and makes a subjective pass or fail judgement based upon their experience and training. The method is time consuming and produces inconsistent inspection results.

Replacement of the human operator with an automatic inspection machine involves overcoming three (3) major obstacles. The first obstacle is to be able to "see" and isolate objects of interest from their background. For instance, gold wires, gold wire bonds, and gold wedges must be identified against gold or similar backgrounds in a manner somewhat similar to that used by a human inspector. The second obstacle is to acquire the image and make pass or fail decisions based upon perceptions of the acquired image. The final obstacle is to repeatedly solve the first two problems at a rate beyond the capability of the human operator.

This invention comprises the combination of a high speed illumination apparatus with a novel image capture subsystem and with other necessary elements for defect fault diagnosis. Apparatus for implementing this invention includes generation of multiple concentric rings of illumination from which light is directed toward the center of the rings. In operation, the area of interest on the microcircuit assembly is placed directly under the focused center of these concentric rings. The angle of incidence for each of these rings is unique, one for interconnect bond wires and ball bonds, while the other is for bond wedges. The combination of both rings is used for isolating microcircuit chips. As light is transmitted via the first ring, an annular layer of illumination is transmitted and focused onto the microcircuit surface from a predetermined angle of incident. Light from this angle of incidence reflects off the specular surface of the bond wires and ball bonds, presenting unique reflective signatures to a dual magnification video cameras system. Similarly, when a second ring is energized, unique reflective signatures on the bond wedges are created. Finally, energizing both of the rings simultaneously, the non-reflective surfaces of the microcircuit chips can be distinguished amongst its reflective neighboring surfaces.

It has been determined that optimal angles of incidence relative to the reflective surface can be found for different classes of objects. Since the reflective surface of the bond wire is cylindrical, for instance, illumination from any angle should produce the same reflective result to the video camera. Limitations arise however, when one has to consider the gold conductor traces the bond wires have to bridge over. These conductor traces form a gold background which have approximately the same reflective angle as the gold wires, thereby causing the bond wires to "disappear" into its background. It is found in this invention that by lowering the angle of transmission to between 75 and 85 degrees from the vertical axis, light reflected from conductor trace surfaces is directed away from the video camera, while the light reflected from part of the cylindrical surface reflects directly to the video camera, providing a significant contrast between the bond wires over the conductive traces.

In the case of the wedge bonds, the physical feature is quite different than that of the cylindrical surface of the bond wire. Its features result from the stamping process in which the bond wire is pressed onto the gold surface by the capillary tube of a typical wire bonding machine. This stamping process flattens part of the cylindrical wire forming a flat reflective surface at the wedge site. This flattened reflective surface changes from the slope angle of the wire to that of the horizontal surface of the substrate. This sloped surface provides a mirror like reflective surface as well as a unique signature compared to that of a bond wire. It is expected that the optimal angle of light transmission will be different relative to the round wire. It has been found in this invention that, by shifting the light transmission angle to between 25 and 35 degrees from the vertical axis, optimal contrast between the wedge reflective surface and the conductive traces can be obtained.

Highlighting the microcircuit chip exclusively from the bond wires, wedges and balls is achieved by using the reflectivity differences between their surfaces. Microcircuit chips have a rough surface and are black in color, therefore, reflects a minimum amount of light. By transmitting full illumination through both ring lights, all areas around the chip are flooded with light while the microchip remains as a dark object. The outline of this microchip is then acquired by the video camera for determination of the chip location, orientation, shape and size as necessary.

Formation of the multiple light rings starts with light generated by a tungsten lamp, collimation by a condenser lens, then passage through a liquid crystal light valve having a plurality of circular active transmission areas. A projector lens receives both rings of light and projects the larger ring on an ellipsoidal reflector which redirects the light onto the microcircuit at the large off-verical axis angle. The projector lens also focuses the more narrow beam of light on a torroidal Fresnel lens mounted above the microcircuit, and which also redirects the beam at the smaller off-vertical axis angle. By alternating the light transmission through each of these rings at high speed, reflective signatures of interconnect wires, ball bonds, bond wedges and microcircuit chips can be captured by the an objective lens and mirror reflected to the light responsive camera system transducers. Based on the known light speed and distances between our transmission source and light responsive cameras, elapsed time between transmission to image capture is calculated to be 3 nanoseconds. Our approach permits the alternating of illumination sources in less than 4 milliseconds using the computer controlled liquid crystal and reflector system. The speed of highlighting microelectronics components is therefore limited by the performance speed of managing illumination transmission through each of the light ring sources.

A dual magnification viewing system was developed using beam splitters and reflectors such that both calibrated high and low magnification images are presented to two separate video cameras at the same time. By selecting the images electronically by the following vision system, the switching of high and low magnification can be obtained in 1 millisecond the high or low magnified images can be acquired in 33 milliseconds.

With the foregoing drawbacks of the prior art in mind, it is a prime object of the present invention to provide a high speed automatic inspection apparatus capable of increasing microcircuit failure detection by improving the contrast between the interconnect wires, ball bonds, bond wedges and chips within a microelectronics assembly from their reflective backgrounds.

It is another object of the invention to provide such contrast improvement when the items to be discriminated are made of a reflective material similar to that of the background, such as gold.

Yet another object of this invention is to provide a first annular concentric ring of illumination which focuses light at a first angle of incidence on centered microelectronic interconnect bond wires or ball bonds, so that their vertically reflected images will be visually sensed with a maximum contrast relative to their similar backgound reflections.

Still another object of the invention is to provide a second annular concentric ring of illumination which focuses light at a second angle of incidence on centered microelectronic bond wedges, so that their vertically reflected images will be visually sensed with a maximum contrast relative to their similar background reflections.

A further object of the invention is to provide two annular concentric rings of illumination, each of which focus light in combination at unique angles of incidence on centered non-reflective microelectronic chips, so that their vertically reflected outline images will be visually sensed with a maximum contrast relative to their backgound reflections.

An additional objective is to provide electronically switched dual fixed magnification subsystems which are faster than a mechanically zoomed single camera.

An additional objective is to provide a precision positioning subsystem for accurate holding of microcircuits under the test optics.

Another objective is to integrate the above illumination elements and other subsystems with machine vision to be operated under computer control.

The above and other objects, features and advantages of the present invention will become more apparent from the following description when making reference to the detailed description and to the accompanying sheets of drawings in which preferred structural embodiments incorporating the principals of this invention are shown.

BRIEF DESCRIPTION OF THE DRAWINGS

The details of my invention will be described in connection with the accompanying drawings, in which.

BEST MODE FOR CARRYING OUT THE INVENTION DESCRIPTION OF MICROELECTRONICS

Figure 1:
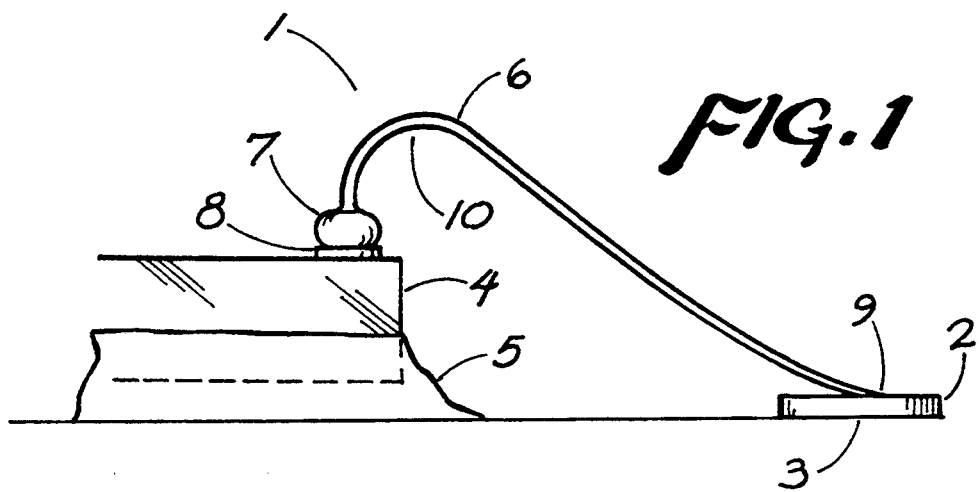
FIG. 1 is a partial side elevation view of a microelectronics assembly, showing a typical interconnection between a microcircuit chip and a conductor trace on a substrate.

Appreciation of the novelty of this invention starts with an understanding of common interconnection methods used in microelectronic assemblies. FIG. 1 is a partial side elevation view of such a microelectronics assembly, showing a typical interconnection between a microcircuit chip and a conductor trace on a substrate.

Figure 2:
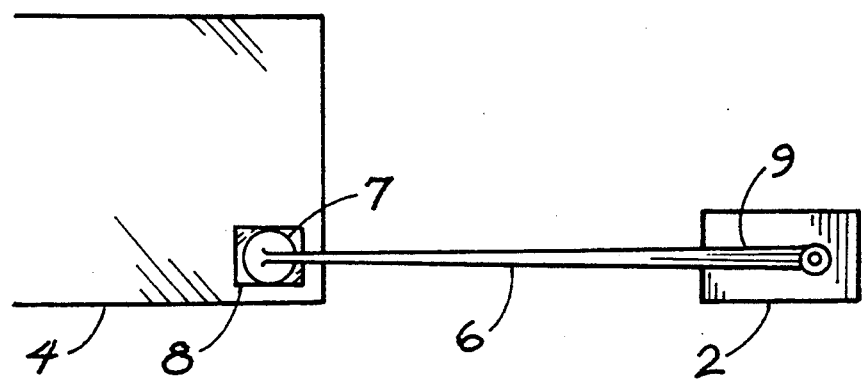
FIG. 2 is a partial top view of the typical interconnection depicted in FIG. 1.

FIG. 2 shows a partial top view of the same interconnection depicted in FIG. 1. Referring to FIGS. 1 & 2, microcircuit assembly 1 generally includes a typical conductive circuit pattern 2 printed on the surface of base substrate 3, usually made of a ceramic material. Microcircuit chip 4 is normally a cube-shaped integrated circuit which is attached onto substrate 3 using conductive or non-conductive epoxy 5. The electrical connection between the microchip circuit and the conductive traces on the substrate is made via cylindrical gold wire 6, typically 0.001 inch in diameter. The attachment of one end of the wire onto the microchip surface takes the shape of a flattened gold ball 7, subsequently named a ball bond. The bonding site for this attachment is called bond pad 8, and normally is a square conductive pad, situated along the edge of microchip 4. The opposite end of wire 6 is attached onto the surface of substrate conductive trace 2 by a stamping process, which results in the form of a flattened wedge 9, subsequently named a wedge bond. Since the surfaces of microchip 4 and the conductive pad 2 are at different heights, the bond wire 6 takes the form of a wire loop 10 between the two connections. This loop assures that bond wire 6 is prevented from touching the edge of the microchip 4, as well as providing adequate stress relief for the bond wire in the event of severe thermal stress and vibrations. Though ball bonds 7, bond wires 6, and bond wedges 9 are unique in their physical shape, they all possess highly specular surfaces. This invention, takes advantage of their specular surfaces and unique reflective signatures, and has provided apparatus and methods for presenting these images to light responsive transducers at high speed.

ILLUMINATION CONCEPTS

Applying known physics principles of reflectivity, we know that for a reflective surface, the angle of reflection is equal to the angle of in incidence, measured from the axis perpendicular to the tangent of the surface. Under usual inspection circumstances, illumination is directed onto the microelectronics surfaces perpendicularly. The light striking the bond wires, ball bonds, and bond wedges scatters in all directions due to their specular and cylindrical surfaces. The gold conductor traces lying in the background also produce scattered light rays, the majority of which are directed vertically back toward the light source because the conductor trace surfaces are relatively flat. These reflected light are the main causes of misinterpretation of images by imaging machines as well as human operators. A key to this invention is the determination of the optimal angles of incidence for the bond wires, ball bonds and wedge bonds, such that maximum contrast between the objects and their neighboring background can be achieved.

Figure 3:
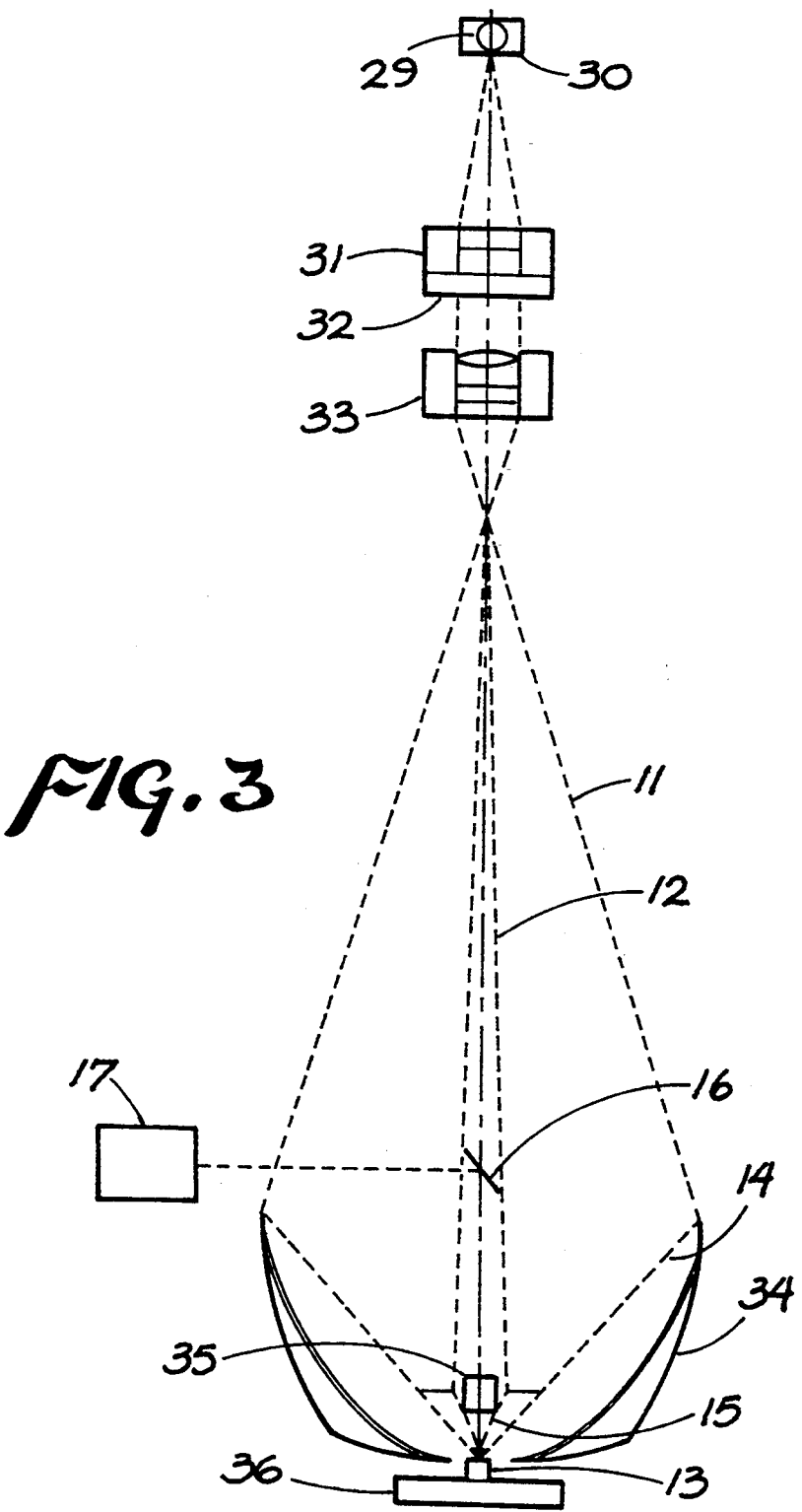
FIG. 3 is an side cross-section view of the microcircuit being illuminated through a liquid crystal light valve and a reflector.

As indicated in FIG. 3, this invention includes two light sources 11 and 12 affixed at the desired angles from the objects of interest 13 such that light rays 14 and 15 striking these objects of interest are reflected to the solid state camera 16 mounted along the vertical axis to the microcircuit. By feeding light into these sources sequentially or simultaneously, different objects can be highlighted respectively. For example, to highlight the bond wires and ball bonds, light 15 at 75 to 85 degrees is illuminated. On the other hand, if illumination of the wedge bonds is desired, the light source 14 at 25 to 35 degrees is illuminated. Similarly, if the chips need to be highlighted, both the lights are illuminated.

The basic optical design of the illumination system is also shown in FIG. 3. Light from lamp 30 is collimated by a cemented doublet condenser lens 31. This condenser lens 31 is positioned one focal length from the lamp, thus collimating the light from the lamps filament 29. The degree of collimation is set by the size of the filament 29.

Figure 4:
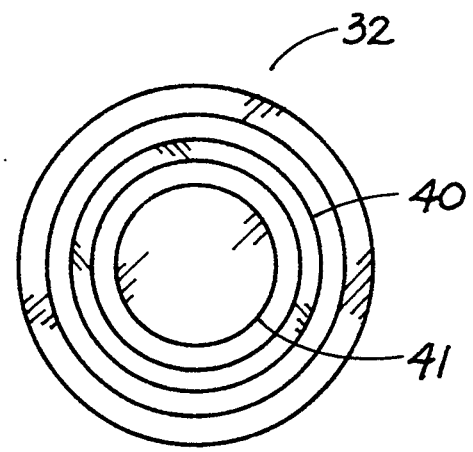
FIG. 4 is a top view of the concentric ringed liquid crystal light valve.

FIG. 4 illustrates a top view of the liquid crystal light valve 32, which is placed just beyond condenser lens 31. Valve 32 has individually addressable concentric circular active regions 40, 41, thus enabling distinct radial zones of light to propagate through the remainder of the illuminator system. The light valve 32 consists of a twisted nematic LCD cell, which has two continuous unpatterned electrodes, and two transmissive polarizing sheets, one sheet acting as polarizer, and two transmissive polarizing sheets, one sheet acting as polarizer, and the other as analyzer, not shown. In the natural state, the liquid crystal cell twists the passing light 90 degrees, however, the twisting power can be nullified by applying an electric field. Therefore, by placing the liquid crystal cell between a polarizer and an analyzer, we have a light valve that can be turned on and off directly by electronic means. The light valve can be made to be in an open or closed mode by arranging the axes of the polarizer and analyzer.

Figure 5:
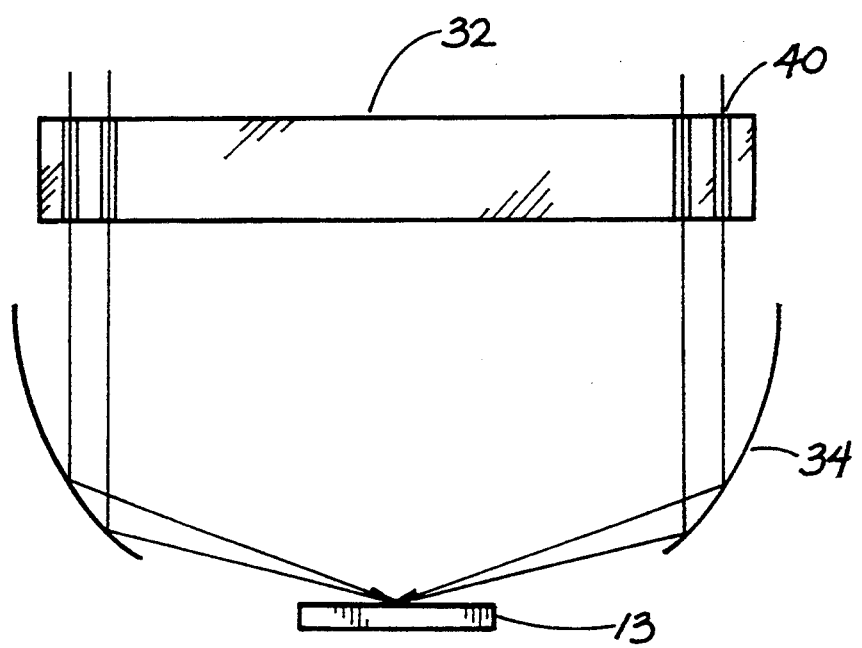
FIG. 5 is a side view of the liquid crystal light valve illuminating the microcircuit at the large off-axis angle via the reflector.

The liquid crystal cell 32 output is imaged by a biconvex and cemented doublet projector lens 33 onto an elliptical reflector 35 and a Fresnel lens 36 which redirects the light onto the microcircuit 13. The function of the projector lens is to image the condenser lens or a plane just in front of it, onto the surface of the ellipse. The light which enters the projector lens 36 is nearly collimated and hence the stop is outside the projector lens. The projector lens 36 therefore takes on some of the characteristics of an eyepiece. The angle of arrival of the illumination light from reflector 35 relative to a normal to the object surface is between 30 and 82.5 degrees. FIG. 5 shows a side view of the light valve 32, arranged to depict the wide angle illumination of ellipsoidal reflector 34 which redirects the beam on microcircuit 13 at the large off-vertical angle. The projector 33 and inner ring 41 have been removed from this view.

The elliptical reflector 35 is not capable of producing angles of incidence less than approximately 50 degrees and hence a second optical system must be used for angles less than 50 degrees. It is mechanically convenient to locate two Fresnel lenses element in a plane just above the objective lens as is shown in FIG. 3.

In summary, the illuminator optical system consists of a cemented doublet condenser lens, a biconvex and cemented doublet projector lens, a parabolic reflector for high angles of incidence illumination and a pair of Fresnel lenses for low angles of incidence. It is capable of illumination angles from approximately 17 to 83 degrees. The optimum angles of illumination can be selected using a liquid crystal light valve. The preferred embodiment light valve consists of three (3) independent rings which are energized by the system controller. As each ring is energized, a ring of light is allowed to pass through the light valve, striking a predetermined location on the reflector. The transmitted illumination is then reflected to the area of interest at the desired predetermined angle. As different light valves are energized by the computer, different angles of illumination on the object can be rapidly achieved, thereby providing significant speed improvement over mechanical shutters.

Using the above angles of illumination and the claimed apparatus, highlighted bond wires have an image signature of a highlighted wire, ball bonds take the shape of a highlighted ball, bond wedges take a lighted shape similar to a triangle and a microchip takes the shape of a black block among white surroundings when projected onto a video monitor via a video camera. By using the threshold function of a machine vision system, the entire wire span can be further isolated from its background.

AUTOMATIC VIEWING SYSTEM

Figure 6:
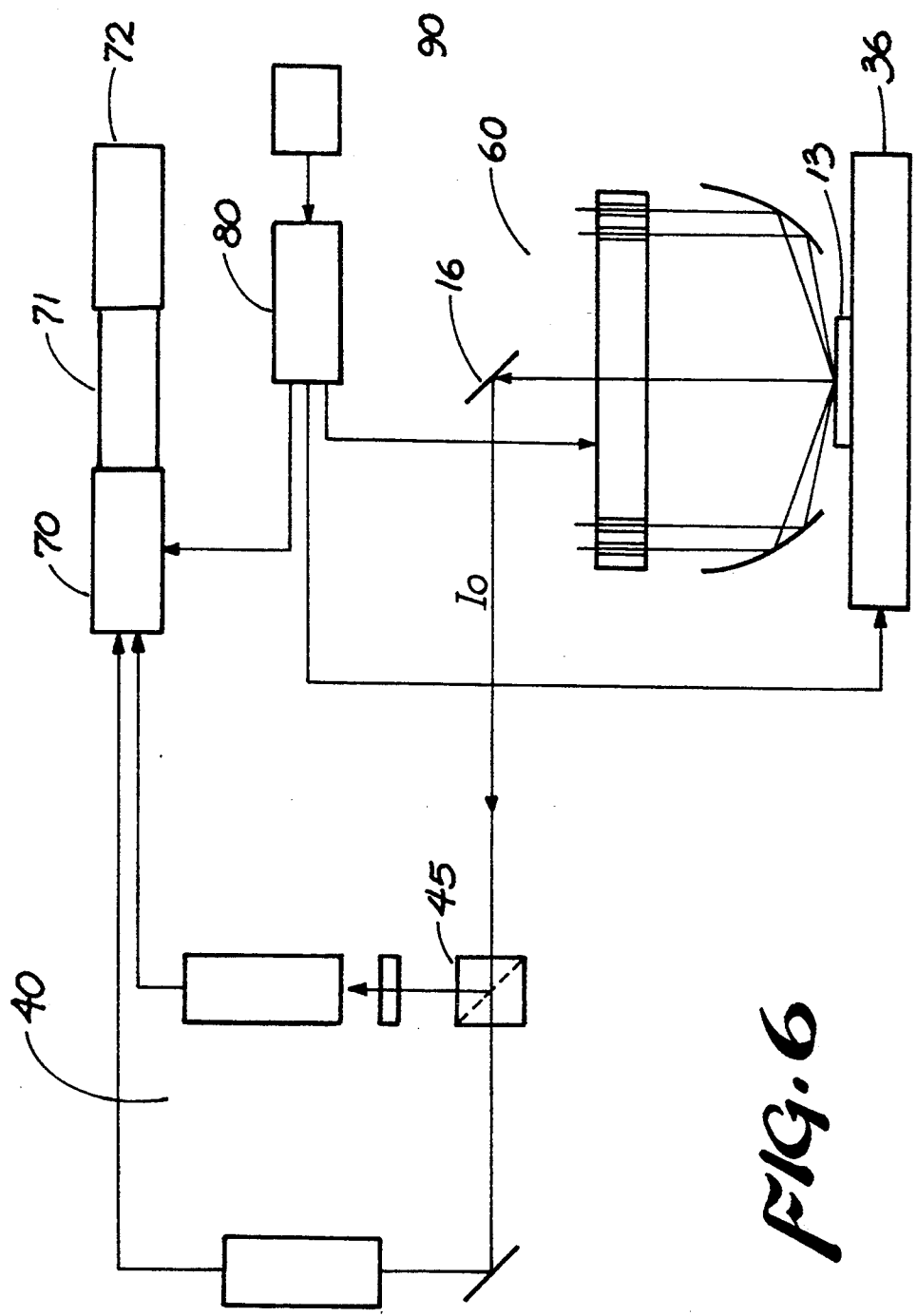
FIG. 6 presents an optical flow diagram of a dual magnification video camera sensor subsystem.

FIG. 6 illustrates the interfacing of the illuminator 60 (shown in part with the large angle light valve/elliptical reflector portion only) with a dual camera sensor system 40, a commercial vision system 70 supported by a video display 71 and printer 72, a three dimensional transport stage 36 for moving the microcircuit 13 under inspection, and a computer controller 80 for operational control under software 90 of all of the above system elements. The following descriptions present an overview of the subsystem designs as built, with a few important constraints and performance parameters indicated. Dual Magnification Subsystem 40

Among the many inspection criteria to be applied by an automatic system, some require a much higher magnification than others. For example, measurement of the diameter of a ball bond requires measurements of the order of 0.003 inches. For reliability purposes, it was determined that a 16 pixel per 0.001" resolution is required. Using a 512×483 CCD camera array, the field of view can be calculated to be approximately 0.3"×0.3". On the other hand, wire separation criteria measures the relative distance of the bond wires from its neighboring wires. In order to view the entire bond wire, a 4 pixel per 0.001" resolution was selected. The field of view is therefore approximately 0.12"×0.12". As illustrated above, a 4× magnification change with precision to about one (1) micron is necessary. A single zooming mechanism with movable parts will have difficulty meeting this stringent requirement.

Figure 7:
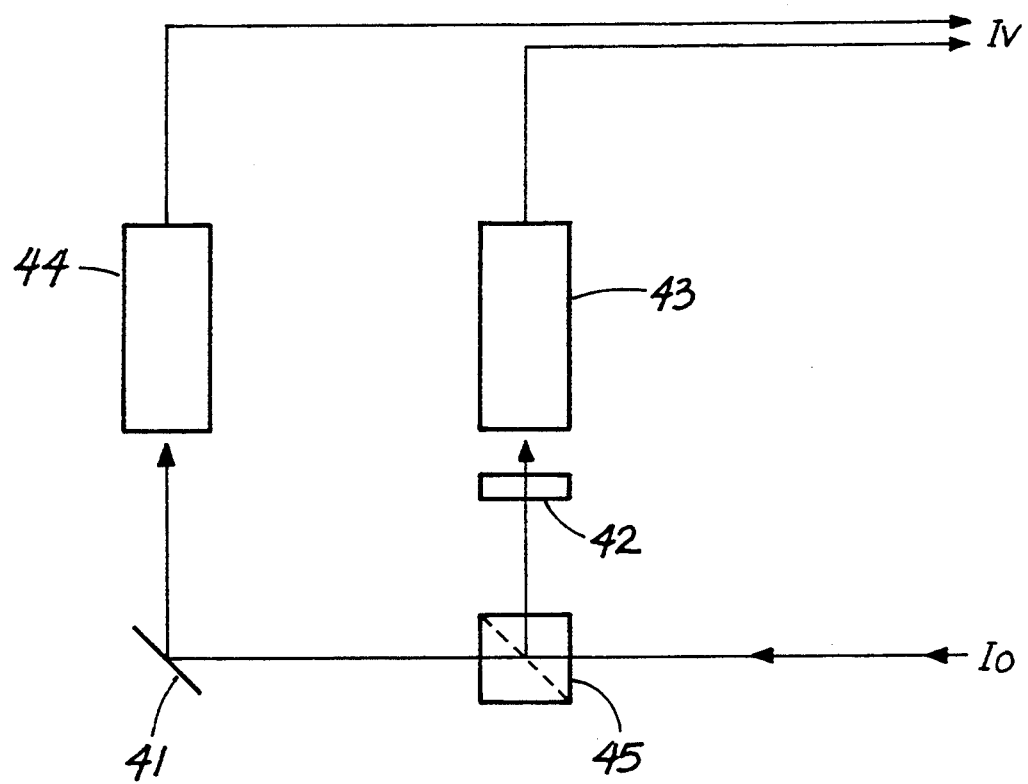
FIG. 7 shows a block diagram of the integration of all major subassemblies into a total automatic inspection system.

A dual magnification viewing system was reduced to practice using beam splitters and reflectors such that both calibrated high and low magnification images are presented to two separate video cameras at the same time. By selecting the images electronically by the vision system, the high or low magnified images can be acquired in about 33 milliseconds. FIG. 7 illustrates the general optical flow of this subsystem. The optical output image Io from the turning mirror 16 of FIG. 3 is received by beam splitter 40, where it is then divided into separate input images for each of the video cameras 43, 44.

The viewing system configuration and size is strongly driven by the illumination system. The minimum distance from the object to the clear aperture of the top of the ellipse is approximately 278 mm. The requirement for a beam splitter to split the high and low magnification image paths increased the total track of the high magnification optical system to approximately 345 mm. The minimum focal length objective was therefore 35 mm for a magnification of 8 times.

The design goals for the low magnification system 42,43 were 4.27×3.12 mm field of view with a resolution of 6.4 microns. The optic lens system as built was comprised of three basic lens groups(not shown); a high magnification objective lens, a field lens group and a relay lens which demagnifies the image from the high magnification viewing system.

The field lens system is comprised of two cemented doublets. The focal lengths of the two achromats of the design were 110 and 206 millimeters respectively. A second micrographic lens with a 20 mm effective focal length was chosen for use as a relay lens. The object and image distances necessary to produce a magnification of 4 times as measured from the metal housing of the lens is 14 and 160 millimeters respectively. At a magnification of 0.25 times the lens was clearly able to resolve objects as small as 20 microns. The overall on-axis optical resolution of the low magnification optical system assuming no degradation by the field lens, was limited to approximately 3 microns. In summary, a dual magnification viewing system has been designed which is capable of near diffraction limited performance without severely restricting the range of illumination angles of incidence has been designed. Testing indicates that the on-axis performance is adequate for the needs of commercial viewing systems.

VME Based Vision System 70

The above system was outputed to a high speed VME based vision system from Data Cube, and was used for image acquisition and processing. In addition, a hardware based SRI algorithm card set developed by Vision System International was also integrated to the Data Cube System. The high processing speed of this set provides sophisticated and accurate information for object tracking, part identification, centroid calculations, orientations, basic dimensioning etc. These seed parameters can be generated in 33 milliseconds per frame. Data such as X and Y dimensions, perimeter, centroids and orientation etc. are produced between 10 to 100 times faster than the traditional software based systems. Therefore, high speed analysis tasks such as microelectronics inspection is a good candidate for its application.

High Speed Assembly Transport Stage 36

Due to the high resolution requirements of the inspection tasks, the areas of interest on the microelectronics assembly must be moved under the optics for inspection. As discussed earlier, the illumination and inspection tasks can be performed within milliseconds, it is important to move the assembly at compatible speeds. Traditional stages using ball slide tables, attached to predetermined pitch screws and motors can be used. By turning the motor electronically, the rotatory motion is translated to a linear motion via the pitch screws. In the embodiment reduced to practice, we designed a belt driven XYZ stage. Each stage was attached to a steel reinforced non-stretchable belt. The belt is driven by a pulley attached to a motor. As the motor is energized, the torque is translated directly to pull the stage along its rails. This approach worked well with a minimum of stiction. The design of the stages consists of single rail structures with precision matching carriers to an accuracy of 1 micron. The entire stage was mounted on a 6" granite surface plate for flatness and stability. High precision glass encoders were used for position reporting to the system controller. High torque to inertia Servo motors are used to maximize the acceleration and deceleration control of the table throughout the inspection cycle. This design resulted in a 0.125 inch movement to the accuracy of 1 micron in 98 milliseconds.

Automatic Inspection Sequence

Figure 8:
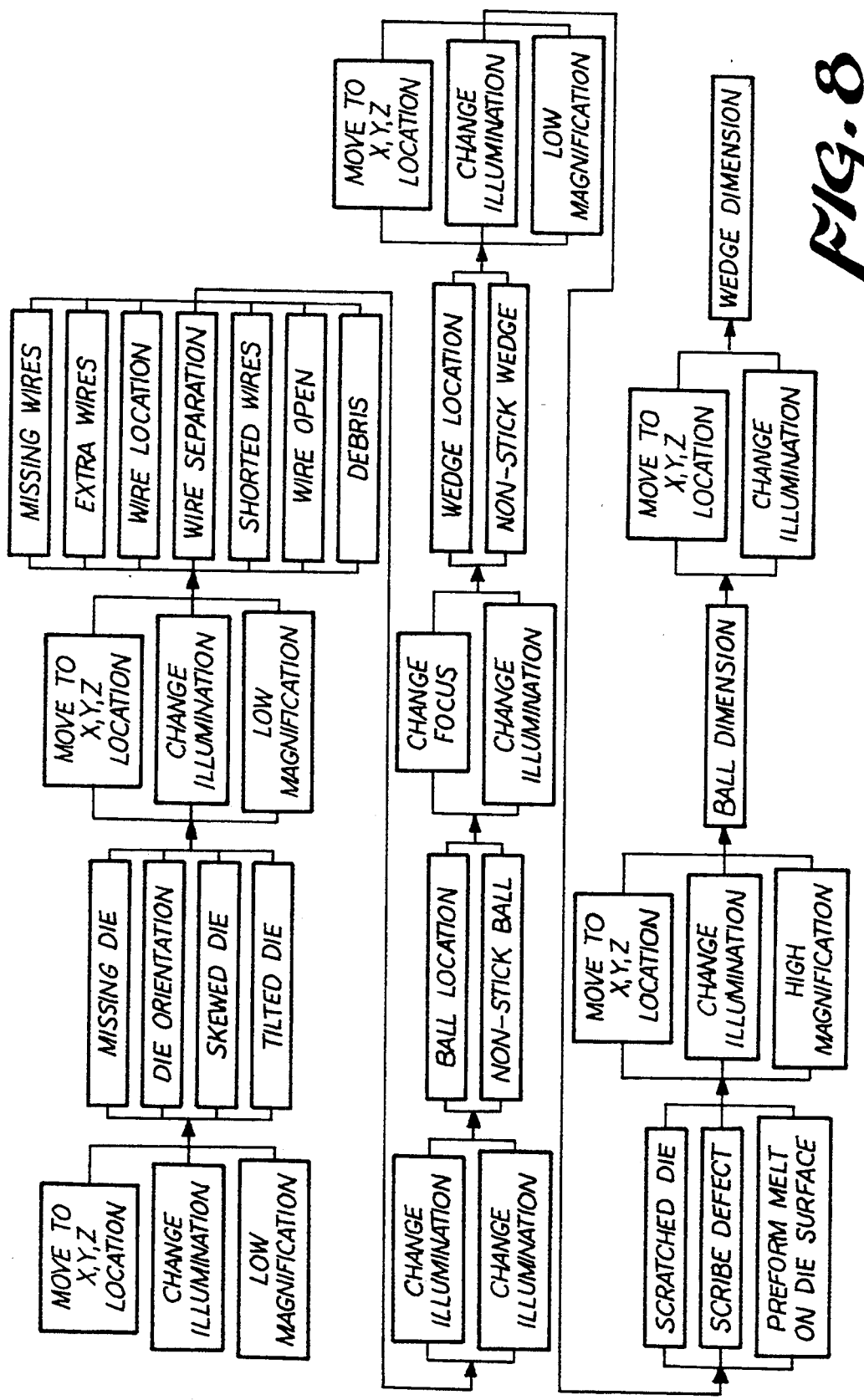
FIG. 8 depicts an inspection flow chart for test determination of 20 microcircuit parameters.

The default inspection logic and flow for dies and wires are illustrated in FIG. 8. However, each be customized by the operator/programmer in the programming mode discussed below. Seven (7) test positions stations, including five (5) table moves, enable measurement of twenty (20) parameters which are necessary in the inspection sequence. Fourteen (14) of the parameters are concerned with potential failure identifications. It will be noted that all of these have been detected without power and before final capping of the microcircuit device.

Operational Software

Figure 9:
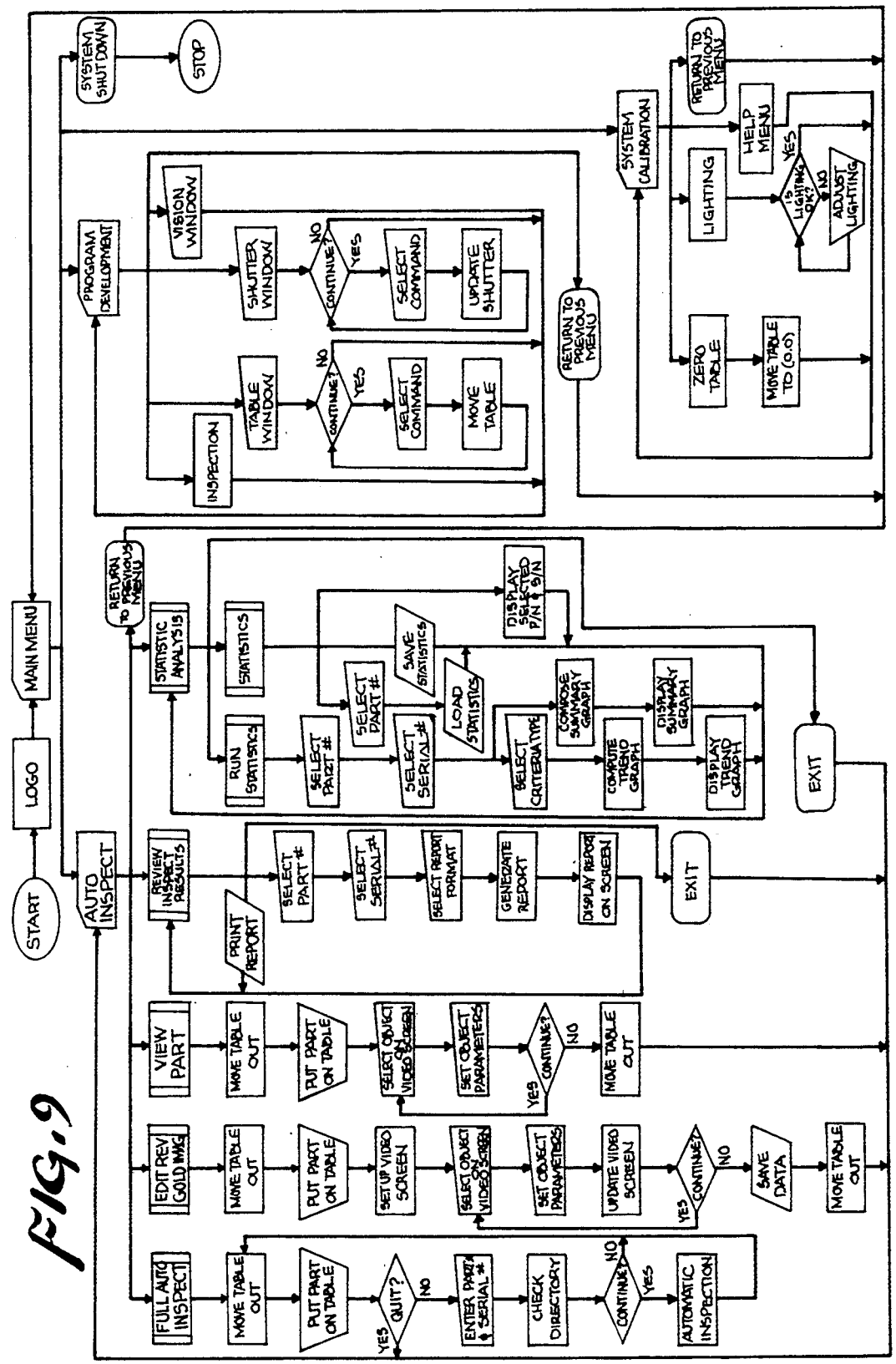

FIG. 9 illustrates a logic flow chart of system operation. Menu driven software has been provided in which operation can be divided into the following modes:

Programming Mode

In this mode, part specific characteristics are programmed into the system for future inspection. The operator is led through the programming routine by point and click mouse driven graphical environment. With the help of the mouse, the operator identifies object to be inspected whether it be a die, ball bond, wedge bond or bond wire. The system will determine the appropriate inspection criteria for the object automatically. The programmer will also be led through the most efficient sequence of inspection for the part. Once acknowledged by the operator, the part specific program is stored in the system based on its part number.

Automatic Inspection Mode

In this mode, the system requests the part number and serial number from the operator. The part specific inspection routine is then loaded into memory. Once the assembly is placed onto the automatic transport stage, the system will perform the pre-determined inspection. Throughout the inspection cycle, the system keeps track of the flaws it identifies and assesses the repairability limits of the part under inspection. In the event that repairability limits are violated, the system will halt the inspection process and reject the part to the operator. The defect data will be written to disk for documentation and future references.

Statistical Analysis

Defect data can be accessed at any time through this software option. Graphical bar and line charts on these defect data can be extracted based on individual part number, single serial number, group of serial numbers, time frame by day(s), week(s), month(s) or year(s). A user has the option to select the statistical results based on the above choices and build a sampling plan for future automatic inspection.

Summary

The above subsystems has been reduced to practice and integrated into a complete machine vision system. Finally, the system has been used to identify 20 defect parameters to date. The particular system control computer and associated software is a matter of design choice. Custom software to support the first 20 defect parameters have been written, however a total package is in continual development.

It should be noted that the system is not limited to inspection of microcircuits only. The high speed illumination technique can be used to control any predetermined illumination for automated inspection systems. By modifying the angle of incident of the illumination, inspection of many other small items having specular surfaces, such as solder joints, component leads, or machine parts can be supported by this invention.

The basic concepts of the techniques and apparatus for providing high speed illumination and the unique signatures of on microelectronics assemblies elements have been illustrated herein. Although the present invention has been described in considerable detail with reference to certain preferred embodiments thereof, other versions are possible. Therefore, the spirit and scope of the appended claims should not necessarily be limited to the description of preferred versions contained herein.

What is claimed is:

1. A system for inspection of microelectronic assemblies having internal microcircuit chips with terminals electrically connected by wire bonding means to circuit conductive traces on a mounting substrate, wherein chip bodies and interconnection elements including wires, ball bonds, and bond wedges which may be visually discriminated against similar reflective backgrounds, comprising:

a plurality of concentric light ring source means for illumination of said chips and interconnection elements placed under the center of each said concentric light ring;

a plurality of focusing means for directing each said light ring source at a predetermined angle of incidence relative to said microcircuit so that optimal contrast is obtained between reflections from said chip bodies and interconnection elements and similar background trace reflections (;), wherein said focusing means comprise:

at least one said focusing means for directing a first said light ring at an illumination angle off vertical which is sufficiently large so as to separate the reflection from rounded inspection objects from conductor background traces made of a similar material;

at least a second said focusing means directing a second said light ring at an illumination angle off vertical which is sufficiently small so as to separate the reflection from inspection objects having variable sloped surfaces from substrate background traces made of a similar material; and first switching means for simultaneously directing said first and second said light rings so as to separate the reflection from inspection objects having flat body surfaces from other substrate and inspection object background reflections;

first optical means for collecting said light reflections from said chip bodies and interconnection elements emanating along a fixed axis through the concentric centers of both said ring lights and for redirecting said reflections for viewing, said first optical means comprising:

second optical turning means for directing said collected reflections away from said concentric center;

a plurality of magnification camera means, each having a separate input magnification lens means, for substantially simultaneous conversion of optical images into electronic signals;

third optical beam splitting means for separating said reflected light from said second optical turning means into a separate optical beams directed to each said input magnification means; and second switching means for activating any selected one or more said camera means to convert said light into said electronic signals; and viewing means for visual inspection of said chip bodies and interconnection elements in order to determine bonding defects.

2. The inspection system according to claim 1, wherein said large illumination angle is between 75 and 85 degrees off vertical.

3. The inspection system according to claim 2, wherein said small illumination angle is between 25 and 35 degrees off vertical.

4. The inspection system according to claim 3, wherein said rounded objects include bond wires and ball bonds.

5. The inspection system according to claim 4, wherein said variable sloped objects include wedge bonds.

6. The inspection system according to claim 5, wherein said interconnection elements and conductor background traces are made of gold.

7. The inspection system according to claim 6, wherein said flat sloped objects include reflective chip bodies.

8. The inspection system according to claim 7, wherein said flat sloped objects further include absorptive chip bodies.

9. The inspection system according to claim 8, wherein a first light ring source is comprised of:

a common source of focused light;

condenser means for collimating light from common source;

light valve means having a first active area means for forming a beam of light having a large beamwidth; and projection lens means for receiving said wide beamwidth of light from said light valve means and focusing said wide beamwidth of light on said first focusing means.

10. The inspection system according to claim 9, wherein said first focusing means comprises an ellipsoidal reflector disposed so as to receive said wide beam of light and to redirecting said beam on said microcircuit at said selected large incidence angle.

11. The inspection system according to claim 10, wherein a second light ring source is comprised of:

said common source of focused light;

said condenser means for collimating light from said common source;

said light valve means having a second active area means for forming a beam of light having a narrow beamwidth; and projection lens means for receiving said narrow beamwidth of light from said light valve means and focusing said narrow beamwidth of light on said second focusing means.

12. The inspection system according to claim 11, wherein said second focusing means comprises lens means disposed so as to receive said beam of light having a narrow beamwidth and to redirect said beam on said microcircuit at said selected small incidence angle.

13. The inspection system according to claim 12, further comprising third light switching means for sequential illumination from each said light ring source.

14. The inspection system according to claim 1 wherein said viewing means comprises a computer controlled machine video system, having stored video reference signals for comparison with said magnified camera means output signals in order to detect video images of defective microcircuit chips and interconnection elements.

15. The inspection system according to claim 1 wherein said viewing means comprises a video monitor for manual viewing of said camera outputs in order to detect video images of defective microcircuit chips and interconnection elements.

16. The inspection system according to claim 1 wherein said viewing means comprises a video monitor for automatic viewing viewing of said camera outputs in order to detect video images of defective microcircuit chips and interconnection elements.

17. The inspection system according to claim 1 further comprising a powered transport stage for adjustable positioning of said microcircuit under test.

* * * * *